United States Patent [19]

Wunsch

[11] Patent Number: 4,559,036
[45] Date of Patent: Dec. 17, 1985

[54] APPARATUS FOR CONTROLLING ADMINISTRATION OF MULTIPLE INTRAVENOUS SOLUTIONS AND MEDICATIONS

[76] Inventor: Richard E. Wunsch, 207 Circle Dr., Traverse City, Mich. 49684

[21] Appl. No.: 561,210

[22] Filed: Dec. 14, 1983

[51] Int. Cl.⁴ .............................................. A61M 5/14
[52] U.S. Cl. ..................................... 604/81; 604/247; 604/250; 604/259
[58] Field of Search ..................................... 604/80–86, 604/65–67, 245, 246, 247, 258, 259, 250; 222/145

[56] References Cited

U.S. PATENT DOCUMENTS

| | | | |
|---|---|---|---|
| 2,954,028 | 8/1960 | Smith | 604/80 |
| 3,043,303 | 6/1962 | Still | 604/66 |
| 4,094,318 | 6/1978 | Burke | 604/81 |
| 4,102,492 | 7/1978 | Gold et al. | 235/375 |
| 4,394,862 | 7/1983 | Shin | 604/67 |
| 4,425,116 | 1/1984 | Bilstad et al. | 604/6 |
| 4,447,230 | 5/1984 | Gula et al. | 604/247 |
| 4,512,764 | 4/1985 | Wunsch | 604/80 |

Primary Examiner—C. Fred Rosenbaum
Assistant Examiner—Karen Kaechele
Attorney, Agent, or Firm—Cullen, Sloman, Cantor Grauer, Scott & Rutherford

[57] ABSTRACT

Apparatus for sequentially dispensing a plurality of solutions through an intravenous supply catheter includes a disposable tubing manifold that is connected to each of the solutions to be administered. Flow of solution through the branches of the tubing manifold is stopped by valves mounted upon a manifold plate which engage each branch. The quantity of solution dispensed is metered by a volumetric infusion pump and controlled by sequentially opening and closing the valves individually. Electronically operable motors or solenoids are connected to each valve for automatically opening and successively closing each valve. A sequencer-timer in accordance with a predetermined program such as from a program card, controls the automatic energization and successive de-energization of each motor, one at a time and successively energizes additional motors for intermittent individual operation through a preselected cycle of machine operation.

12 Claims, 4 Drawing Figures

APPARATUS FOR CONTROLLING ADMINISTRATION OF MULTIPLE INTRAVENOUS SOLUTIONS AND MEDICATIONS

BACKGROUND OF THE INVENTION

1. Technical Field

The present invention relates to apparatus including a manifold for automatically administering intravenous solutions and medications. More particularly, the invention relates to apparatus for sequentially supplying a plurality of solutions to a single intravenous tube.

2. Prior Art

Medical treatment frequently requires the administration of more than one solution or medication by intravenous injection. In many medical treatments several drugs are administered periodically.

To minimize the number of injections given to a patent it is common practice to inject medications through a single intravenous tubing by means of one or more Y-connectors. The normal procedure is for a member of a hospital staff to unsheath a needle and insert it in a Y-connector at time periods and in quantities specified by the treating physician. When a given medication has been administered the needle is removed from the Y-connector, resheathed and stored next to the patient's bed until the next treatment interval. This procedure is subject to contamination due to the repeated sheathing and unsheathing of the needle. While this procedure is acceptable when a limited number of medications are administered, as the frequency of administration increases the amount of staff time expended, difficulty of keeping the needle and Y-connector sterile, and chance of error in administering a medication likewise increase.

This procedure for periodically administering medications to patients is time consuming for hospital staff and requires detailed instructions because medication is often prescribed around the clock. In medical treatments requiring a large number of solutions each having a loosely hanging tube, a member of the hospital staff could conceivably be confused and dispense the wrong solution.

Frequently, tubes are left dangling loosely around the patient's bed, instead of being tied out of the way, because the tubes must be free for connection to the Y-connector. The tubes can be caught in the side rails of the bed and damaged. During administration of a solution one of the tubes may be pinched off inadvertently resulting in insufficient medication being dispensed.

Various types of manifolding apparatus having been developed to meet the problems posed by supplying multiple medications to a patient. U.S. Pat. No. 2,954,028 to Smith discloses such an apparatus for administering parenteral fluids through the use of a manifold. While the Smith manifold allows a large number of medications to be administered simultaneously, it is bulky and time consuming to set up. The different medications in the various passages of the manifold may intermix and if not compatible could interact deleteriously with each other. Different branches of the manifold open into the central tube at directly opposite locations which allows the fluids to flow from one branch into another.

Reuse of the Smith manifold is subject to several drawbacks. It is well known that some medications, while theraputic for some, are toxic to other patients. If a patient receives medication through a manifold residual deposits of a previously administered medication may be present in the manifold. If the residual deposit is a substance that is toxic to the patient it is possible that the patient could be harmed. Therefore, unless the manifold is cleaned and sterilized between each patient, there is a danger that a patient may inadvertently receive residue from a medication administered to a prior patient. Cleaning and sterilizing the manifold between uses is laborious and requires valuable staff time.

In addition, prior art devices have failed to disclose an accurate method for sequentially metering several different medications through a common catheter that is both inexpensive and simple to use. While visual sight glass drop counters have been used with Y-connectors, as shown in U.S. Pat. No. 3,886,937 to Bobo et al and in the Smith manifold described above, such devices are time consuming to use and must be visually monitored for accuracy. Electronic drop counters as disclosed in U.S. Pat. No. 4,094,318 to Burke offer improved accuracy but are extremely expensive, expecially if more than one or two solutions are to be administered.

RELATED PATENT APPLICATION

Applicant's copending U.S. patent application, Ser. No. 423,978 filed Sept. 27, 1982, now U.S. Pat. No. 4,512,764 is entitled "Manifold For Controlling Administration of Multiple Intravenous Solutions and Medications". The manifold includes manually operated valves for individually controlling the flow of each fluid through the manifold. The time intervals for opening and enclosing each valve are manually controlled.

The difficulty is that an operator must attend to the manual operation for opening and closing the valves individually and one at a time and at the same time determine the period that each valve is open. Also the attendant must make sure that the valve which controls the flow, or interruption of flow of the TKO or the keep open basic solution, must be so manually regulated, so that the valve is open when all other valves are closed for continued intravenous feeding of a neutral or basic solution or medication to avoid clotting or clogging of the catheter or intravenous needle. It is further required to intermittently open the TKO valve between the opening and closing of any two other valves to be sure that there is a flow of neutral solution between the flows of different solutions out through the manifold to eliminate any remnants of solution from one source mixing with a second solution.

In the copending application, the multiple intravenous solution manifold comprises a three-piece manifold valve assembly having a disposable tubing manifold that assures sterility and purity in medications. The three part manifold apparatus is simple to disassemble for removing the disposable tubing manifold and replacing it with a new sterile tubing manifold. The remainder of the manifold valve assembly does not contact any medication and therefore may be safely used repeatedly by different patients.

In the copending application, the manifold plate has a plurality of manual valves with each valve being operative to close off the flow of a solution through a branch of the tubing manifold to control the flow of the solutions to the patent.

In the copending application, the dispensing tube of the valve manifold is preferably connected to an infusion pump that in turn pumps the intravenous solution at a measureable rate into a patient by means of an intravenous needle or catheter. At any one time it is preferred that ony one valve will be open to allow the solution to be accurately measured as it is dispensed. The infusion pump draws solution at a known flow rate for a prescribed period of time, whereby the medication dose may be easily and accurately measured. A tube from a keep open solution, or base solution, is connected to one end of the valve manifold for use when no medication is being dispensed to prevent the formation of clots in the catheter or in the patient's vein at the injection point and is further used between the dispensing of different medication solutions to prevent mixing of the medications.

SUMMARY OF THE INVENTION

An important feature of the present invention is to provide reversible electric motors or motor means including electronically controlled solenoids connected to the individual valves by which the valves mounted upon the valve plate may be automatically opened and closed intermittently energizing and successively de-energizing the electric motor means.

Another feature is to provide in connection with the manifold and its branches to which are directed various fluids to be injected intravenously, a valve for each branch of the manifold and for the inlet to the manifold for the purpose of squeezing closed adjacent portions of the manifold tubing preventing the flow of any of the fluids through the manifold. The valve includes a retractable element having a normal advanced position of maintaining the corresponding tube portion collapsed. Upon operation of an electric motor means, such as a reversible motor, or a solenoid is adapted to retract the valve element of the valve for a predetermined period to permit the passage of intravenous fluid in one of the branches or through the inlet of the manifold for a predetermined period. Either reversal of the motor or the deactivation of the solenoid causes the valve element to re-engage and close off the corresponding tube portion of the manifold or manifold branch stopping further flow through that branch.

Another feature includes an electronic controllable sequencer-timer having a plurality of electrical output leads connected to each motor means for individually and progressively activating one motor means opening said valve and after a predetermined time interval deactivating said motor means successively for closing said valve. Further progressively in accordance with a predetermined time interval activating another motor means successively opening a valve for further progressively in accordance with a predetermined program successively activating and deactivating singly additional motor means.

A further feature includes in conjunction with an electronic controllable sequencer a timing cycle wherein over a period of time corresponding valves are independently and successively opened for a predetermined time interval and thereafter closed wherein successively an additional valve is separately opened for a period and successively wherein throughout the complete cycle each of the individual valves are progressively and one at a time opened for a period maintained open and successively closed. As a result the administration of the respective different intravenous fluids continues one at a time automatically throughout the cycle or repeats thereof during the overall time cycle for the machine.

Another feature of the present invention contemplates that each valve will include a movable element in one position normally squeezing together an adjacent portion of the tubing of the manifold preventing the flow of any particular intravenous fluid through a corresponding branch of the manifold and wherein automatic control mechanism is provided whereby only one valve will be opened for a period, maintained open and successively closed before a second valve is opened for a predetermined period and successively closed, etc.

A further feature contemplates the use of a program card impressed with a predetermined program or input data which is removably projected into the sequencer-timer for the progressive energization and successive de-energization of the multiple channel output from the sequencer-timer individually connected to the corresponding motor means.

A further feature includes a miniaturized reversible electric motor mounted upon each valve which includes a drive shaft wherein the movable element is actuated by a valve stem threadly connected thereto and wherein intermeshing gears are interposed between the drive shaft and the valve stem whereby in an automatic manner the valve may be opened for a predetermined period, thereafter progressively closed. Upon deactivation of a first electric motor, a second electric motor is activated, etc., opening another valve for a predetermined period of time and thereafter rotating in the opposite direction for closing the valve.

A further feature includes in conjunction with each of the valve elements a spring biased piston attached thereto and a solenoid having a reciprocal armature connected to the piston whereby on selective energization of the solenoid, the element is retracted for a predetermined period of time opening the passage of one fluid through a branch or portion of the manifold. Upon deactivation of the solenoid the element is biased in the opposite direction for closing off the flow through said branch or manifold.

A further feature contemplates the use of a hinge interconnecting the one side edges of the manifold and valve plates, and with a screw means interconnecting the other side edges of said plates for facilitating opening of the manifold plate and for replacement of the tubing manifold.

An important feature includes in conjunction with an electric controllable sequencer-timer, a program card having thereon a plurality of markable parallel spaced tracks corresponding to the number of controlled channels to the respective electric motors. The tracks have a length corresponding to a preselected time cycle with preselected data applied to each track. The sequencer-timer includes a solid state random access memory activated by the incoming data upon the program card together with a plurality of output switches corresponding and connected to each channel respectively for selectively and progressively activating one at a time, each motor means in compliance with data programmed upon the input program card.

These and other features and objects will be seen from the following Specification and claims in conjunction with the appended drawings.

THE DRAWINGS

It will be understood that the above drawings illustrate merely preferred embodiments of the invention and that other embodiments are contemplated within the scope of the claims hereafter set forth.

DETAILED DESCRIPTION OF AN EMBODIMENT OF THE INVENTION

Figure 1:
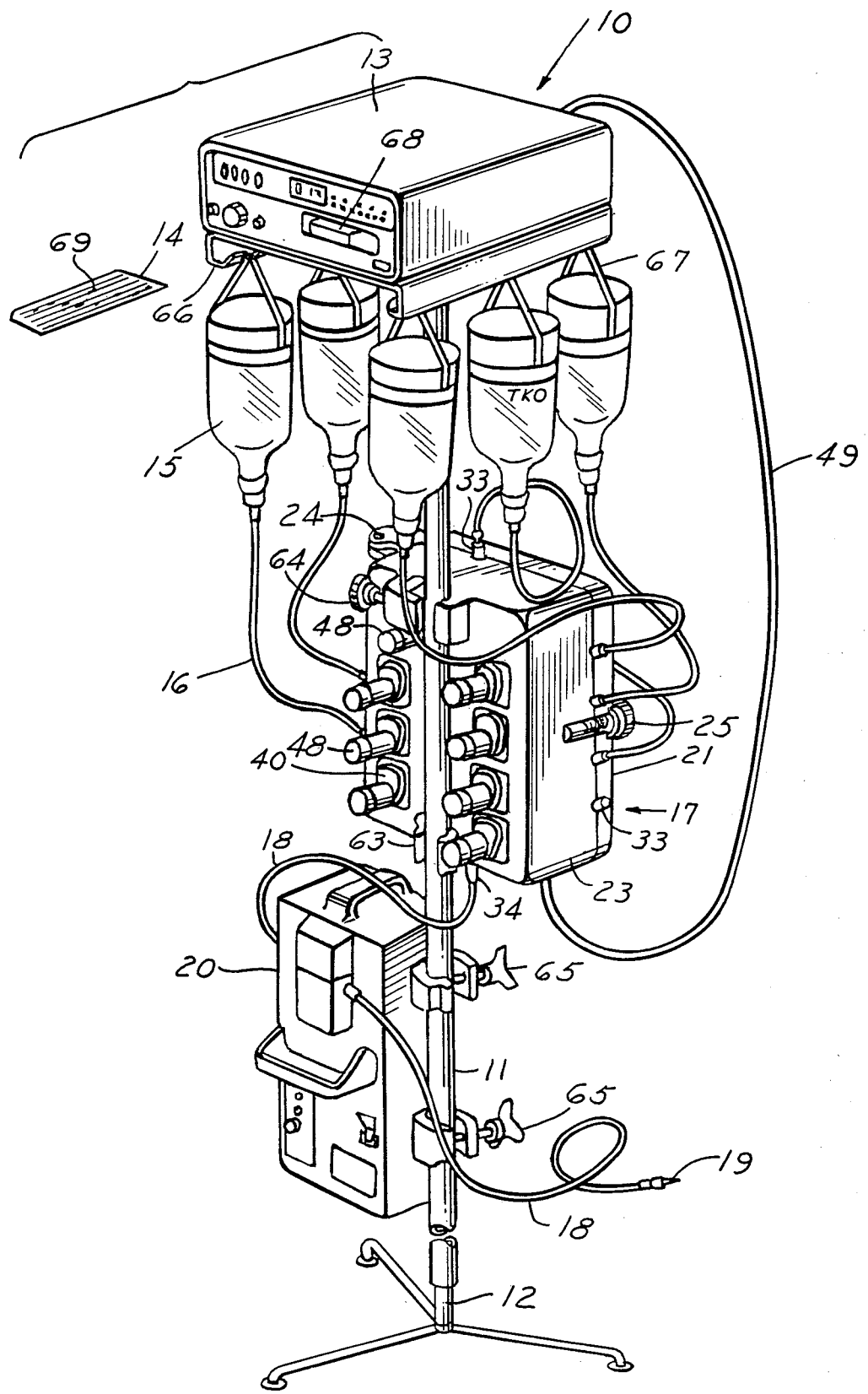
FIG. 1 is a front perspective view of the present apparatus for controlling administration of multiple intermediate solutions.

Refering to FIG. 1, apparatus for controlling the administration of multiple intravenous solutions and medications is generally indicated at 10 for intravenously dispensing a plurality of medications and solutions to a patient. An upright vertically adjustable tube support 11 is mounted upon a standard post 12, fragmentarily shown.

Electronic controllable sequencer-timer 13 overlies tube support 11 and is suitably bracketed thereto. The sequencer-timer 13 has a plurality of electrical output leads 49 connected to each motor or motor means, hereafter described, to individually and progressively activate one motor means opening a valve and after a predetermined time interval, deactivating or reversing the motor means for successively closing said valve and for further progressively and in accordance with a predetermined program successively activate and deactivate similarly or reverse additional motor means.

In the illustrative embodiment, the controller sequencer-timer is a unit available on the market. For example, one such timer is known as the XANADU Controls-Solid State Programmer Sequencer. XANADU Controls, of Springfield, N.J., is a division of Valcor Engineering Corporation.

The structure, function and operation of the controller sequencer-timer is set forth in U.S. Pat. No. 4,102,492 dated July 25, 1978 entitled Universal Programmable Process Control Apparatus. To the extent that the function and operation of the controller sequencer-timer is not shown in detail in the drawings herein, such portions thereof as directed to the function and operation set forth in said patent are incorporated herein be reference.

In the illustrative embodiment employing the present disclosed controller sequencer-timer 13, there is incorporated a program card 14, FIG. 1, which is mountable upon a retractable tray 68. The tray 68 projects from the sequencer-timer 13 to receive the program card 14.

A plurality of intravenous fluid bottles 15, sometimes hereafter referred to as I.V. bottles, each contain different medications or solutions adapted to be delivered through corresponding supply tube 16 to the present solution manifold selector 17 mounted upon support post 11 in FIG. 1. One of the IV bottles has a further designation TKO thereon, representative of Keep Open Base Solution, which in accordance with a predetermined sequence hereafter described and through its supply tube 16 is directed to the present solution manifold selector 17. Depending from the solution manifold selector 17 at 34 is a flexible dispensing tube 18 which has on one end a catheter or intravenous needle 19.

Needle 19 is adapted for application to the vein of a patient, human or otherwise, for the controlled delivery of a plurality of different intravenous solutions or medications, one at a time. This is determined by the solution manifold selector 17, which may be automatically controlled by the sequencer-timer 13.

In the illustrative embodiment, and to assist in the uniform delivery of preselected different intravenous fluids to the patient, there is employed an infusion pump 20, readily available on the market, which is interposed in the dispensing tube 18 for pumping solutions, one at a time, into the patient at a predetermined flow rate as set by the pump 20. The manifold selector includes manifold plate 21, replacable manifold 22 and a valve plate 23 sandwiched together, as shown in FIG. 1, and is shown further in FIG. 2 corresponding to the drawing in copending application Ser. No. 423,978.

The valve plate 23 of my copending application corresponds to valve plate 23 forming a part of the present solution manifold selector 17, FIG. 1. The only difference is that the valves 40 in the copending application are manually operable while the valves 40 of the present embodiment, FIG. 1 are controlled by electric motor means. These are either reversible electric motors 48, FIG. 3, or solenoids 59, FIG. 4, for individually controlling the operation of the respective valves 40.

Where in the copending application, the manifold plate 21 is connected to the valve plate 23 with the tubing manifold 22 interposed in a sandwich, as by fasteners extending through the corresponding plates, in the illustrative embodiment, FIG. 1, the assembly of the manifold plate 21 to the valve plate 23 includes upon their one upright sides a hinge 24 and upon their other upright sides, the hand operated screw fastener 25. By this construction, manifold plate 21 may be swung open upon release and disengagement of fastener 25 to permit the removal and replacement of tubing manifold 22, FIG. 2.

In operation, the intravenous solutions contained in the plurality of bottles 15, including the bottle marked TKO, are connected to the manifold 22 by means of supply tubes 16. The solutions passing through the manifold 22 are sequentially administered by means of the dispensing tube 18 which is powered and controlled by infusion pump 20. The medication is injected into a patient by means of a catheter or intravenous needle 19. It is contemplated that an intravenous needle is considered equivalent to the use of a catheter.

Manifold plate 21 which receives the tubing manifold 22 is covered by the valve plate 23. Manifold plate 21 as described in said copending application is a rigid member having a vertical slot 26 running the length of the manifold plate from the top 27 to the bottom 28. The vertical slot is a U-shaped channel opening on the face of the manifold plate. Branch slots 29 are formed in the manifold plate 21 to extend from the vertical slot 26 to the lateral sides 30 of the manifold plate. The branch slots are U-shaped channels that open into the face of the manifold plate. The branch slots 29 extend upwardly from the vertical slot 26 at a slightly acute angle.

The tubing manifold 22 is made up of the trunk tube 32 that extends from the top 27 to the bottom 28 of the manifold plate. The trunk tube 32 includes a female connector 33 on its top end and a male connector 34 on its bottom end. A plurality of branch tubes 37 extend from opposite sides of the trunk tube 32 from longitudinally spaced openings 38 formed in the trunk tube. The branch tubes open into the trunk tube 32 to permit fluid flow from the branch tubes 37 to the trunk tube 32. The branch tubes intersect the trunk tube at spaced locations to that fluid flow is directed into the trunk tube and not into another branch tube. An upper portion of trunk tube 32 is sometimes referred to as a branch.

When the tubing manifold 22 is placed in the manifold plate 21, the branch tubes 37 are fit into the branch slots 29 while the trunk tube 32 fits into the vertical slot 26. The branch tubes 37 in their free state extend perpendicularly from trunk tube 32. However, when the tubing manifold 22 is placed in the manifold plate 21, the branch tubes 37 are bent into the inclination of the branch slots 29. By doing so, fluid flow in the branch tubes from the lateral sides 30 to the trunk tube 32 is encouraged by gravity while fluid flow in the opposite direction is resisted by gravity.

The valve plate 23 includes a plurality of valves 40 which are used to selectively permit fluid flow through the branch tubes 37 and the trunk tube 32. The valves 40 includes a reciprocal element 41, FIG. 3, which is positioned to bear upon one of the branch tubes 37 or the trunk tube 32. The element, sometimes referred to as a wedge, is connected to internally threaded valve stem 42 that is retained in the valve plate by mount plate 46. The valve stem receives valve shaft 43 for moving the element longitudinally relative to the internally threaded valve stem 42. Element 41 is slidably and non-rotatively movable in flat slot 44.

Figure 2:
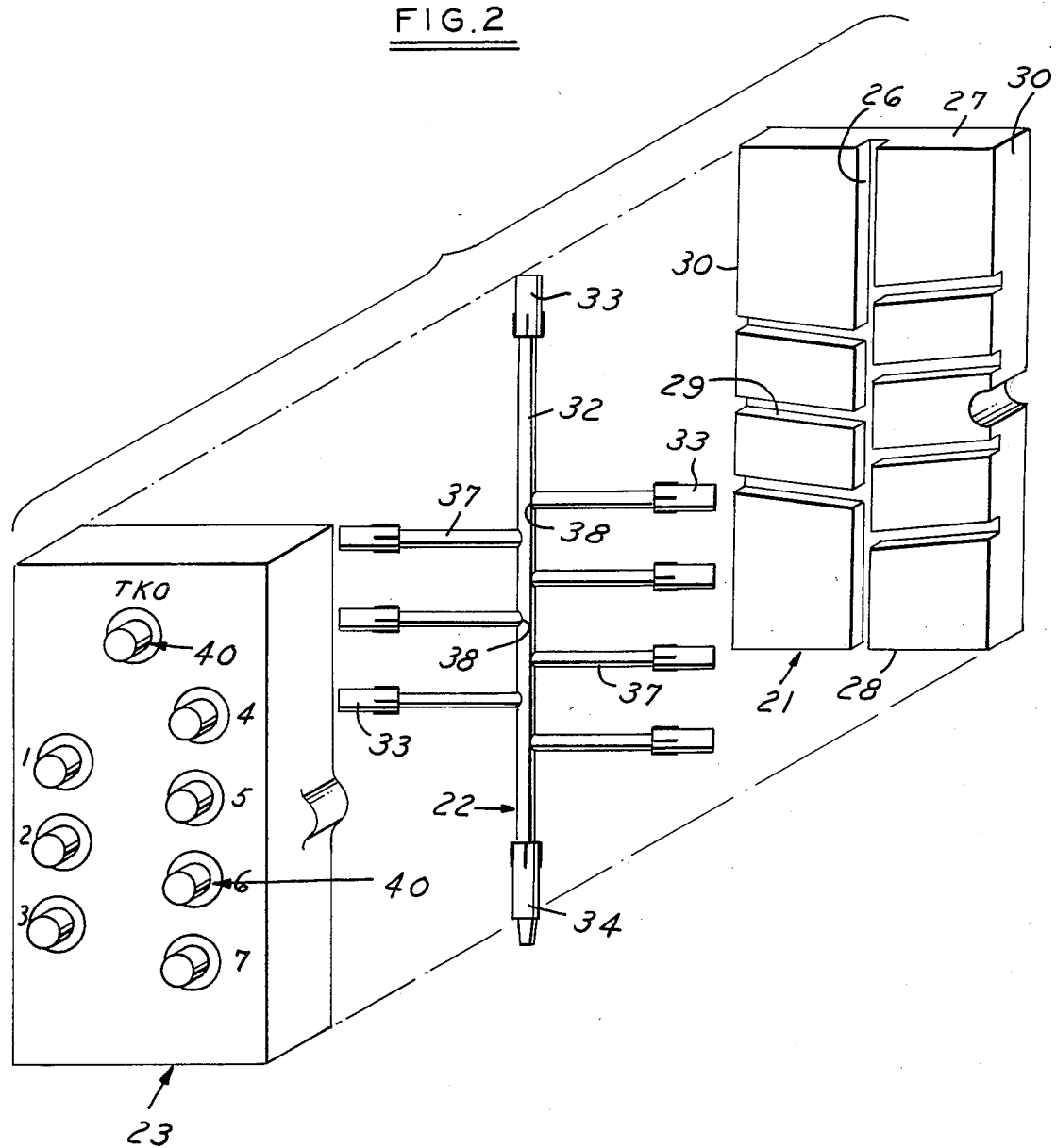
FIG. 2 is an exploded perspective view of the elements of the solution manifold selector and tubing manifold shown in FIG. 1 and on an increased scale.
Figure 3:
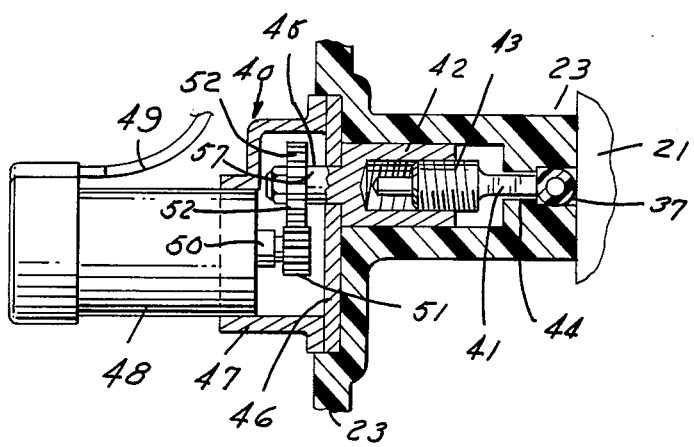
FIG. 3 is a fragmentary longitudinal section of a reversible motor operated valve of which a plurality are shown in FIG. 1, mounted upon the manifold selector on an increased scale.

Each of the valves 40 has an open position, FIG. 3, in which fluid flow is permitted through the tube or branch 37, and a closed position in which the element 41 is pressed against tube 37 to prevent fluid flow therethrough. A valve 40 is also provided adjacent the trunk tube 32 for shutting off the keep open solution from the bottle marked TKO, FIG. 1. The valve 40, FIG. 2, marked TKO, engaging the trunk tube 32 operates in the same manner as each of the valves 40 engaging the branch tubes 37.

In operation, the solution bottles 15 are hung above the manifold selector 17, such as from sequencer-timer 13, so that solutions flow from the bottles 15 to the selector 17 through the supply tubes 16. One supply tube is received within the female connector 33, FIGS. 1 and 3, that extends from the top 27 of the manifold plate 21 in fluid flow connection with the trunk tube 32. Other supply tubes 16 are received within female connectors 33 that are attached to each of the branch tubes 37 and extend from the lateral sides 30 of the manifold plate 21. Each I.V. solution flows from the bottles 15 to the manifold selector 17. The flow of the I.V. solution into the dispensing tube 18 is controlled by means of the valves 40. Each of the valves 40 has an open position in which fluid is permitted to flow from the supply tubes 16 into the dispensing tube 18 and a closed position in which the branch tube 37 or trunk 32 is pinched off to prevent fluid flow therethrough.

As disclosed in my pending patent application Ser. No. 423,978, fluid volume through the dispensing tube 18 is controlled by volumetric infusion pump 20. The pump 20 accurately meters and maintains constant flow through the dispensing tube and can regulate the amount of fluid administered. By controlling the amount of fluid administered while the appropriate valve 40 is open the volume of solution dispensed is automatically controlled.

Accurate control of fluid administration may be assured by sequentially opening and closing the valves 40 so that a single volumetric infusion pump may be used to draw fluids from each of the solution bottles sequentially. When none of the medications are required the valve 40 controlling the trunk tube 32 is opened to permit the keep open solution TKO or base solution to flow, thereby keeping the intravenous needle open and free of clots. The valve 40 for the keep open solution is preferably opened for a short period between changes in medication to flush out the manifold, thereby preventing intermixing of solutions.

According to the present invention the tubing manifold 22 is disposable. The manifold plate 21 is easily opened from the valve plate 23 and the tubing manifold may be simply disconnected from the supply tubes 16 and removed from the manifold selector 17. The tubing manifold 22, FIG. 2, is then replaced when a new patient is to be hooked up to the manifold selector 17.

As disclosed in my copending application, up to eight solutions may be accomodated by a single manifold selector 17. It should be understood that the number of branches and valves provided can be changed. Each of the fluids is introduced into the trunk tube at a location spaced from the other openings 38 in the trunk tube 32. In this way the fluids are introduced into the trunk tube 32 and begin flowing toward the bottom 28 of the manifold plate 21 before encountering the next opening 38 in the trunk tube 32.

Referring to FIG. 3, internally threaded valve stem 42 includes an axial shank 45 which extends through mount plate 46 and into gear housing 47 forming a part of valve assembly 40. The miniature, reversible electric motor 48 having a power lead 49 at one end is projected into and secured within gear housing 47 and includes drive shaft 50. The channel lead is one of a plurality of channel leads designated at 49 in FIG. 1, which extends from the sequencer-timer 13. In the illustrative embodiment, there are eight channel leads which extend from the sequencer-timer 13 and which are individually connected to the electric motor means 40, 53 FIGS. 3 and 4.

A pinion 51 on shaft 50 is in mesh with gear 52 mounted upon shaft 45 of valve stem 42. With positive voltage delivered through channel lead 49 to motor 48, drive shaft 50 will rotate in one direction for effecting a retraction of valve element 41 releasing branch 37 from its collapsed condition and permitting the flow of fluid therethrough. The branch 37, FIG. 3, corresponds to the branches 32, 37 of FIG. 2.

In FIG. 3, motor 48 has been activated by a positive voltage retracting valve element 41 to permit flow of fluid through branch 37. After a predetermined time interval, negative voltage is delivered through lead 49 to motor 48 for rotating the drive shaft 50 in the opposite direction. This causes a longitudinal advance of the valve element 41 to operatively engage and collapse an adjacent section of the branch tube 37 closing off flow therethrough. This will be the normal condition of the valve assembly 40 with flow through tube 37 closed.

Figure 4:
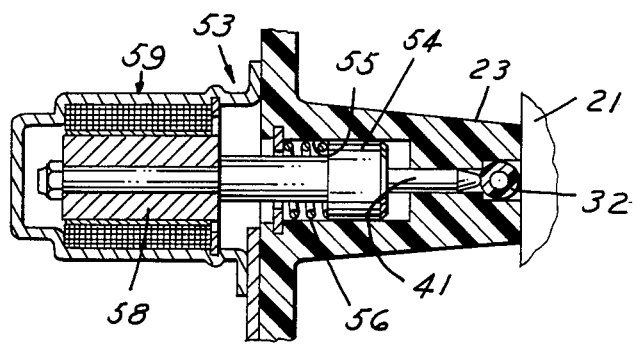
FIG. 4 is a similar fragmentary section, showing a solenoid controlled valve corresponding to the valves shown in FIG. 1.

With respect to the electric motor means associated with the valve assemblies 40, instead of using a reversible motor 48, there may be employed solenoid valve actuator 53, FIG. 4. In this embodiment, valve element 41 is shown in a retracted open position and wherein the solenoid 59 of the actuator 53 has been energized through a corresponding lead 49, FIG. 3.

Piston 54 is axially connected to element 41 and is positioned within a cylindrical bore 55 within mount plate 23, fragmentarily shown. Coiled spring 56 is nested within the bore 55 and is retained by stop ring 57.

The spring 56 is adapted to normally bias the element 41 to an advance position wherein the element 41 crushingly engages and collapses the corresponding branch 32, FIG. 2 for illustration, or any of the branches 37 for interrupting the flow of intravenous fluid therethrough.

The solenoid valve actuator 53 also includes armature 58 shown in a retracted position, FIG. 4, with solenoid 59 activated.

Forwardly facing tube guide 63 located upon the front face of valve plate 23 extends around portions of tube support 11 in cooperation with the manually adjustable tube clamp 64 on the valve plate 23 for adjustably securing the solution manifold selector 17 in a predetermined position.

A pair of vertically spaced hand clamps 65 project laterally from the infusion plump 20 and are adjustably received upon support tube 11 for clamping infusion pump 20 in a preselected adjusted position thereon.

Depending from the controller sequencer-time 13 is a suitable support bracket 66 which includes a clamp means, not shown, centrally thereof which overlies and is secured to the upper end of tube support 11. Each of the bottle 15 includes a swivel type of bottle holder 67 which is removably connected to the corresponding opposed support brackets 66, by which the bottles 15 are removably suspended from sequencer-timer 13. The support standard post 12 has a base of sufficient lateral extent so as to stabilize and maintain the entire assembly, in FIG. 1 adjustably secured upon tube 11.

As shown in FIG. 1, there is provided upon sequencer-timer 13 upon the front thereof the retractable tray 68 upon which is positioned the program card 14. The card 14 has thereon a plurality of data receiving parallel spaced tracks 69.

With respect to the programmer timer 13 whose structure, function and operation are disclosed in U.S. Pat. No. 4,102,492, specific details of the construction thereof are omitted, except to the extent that operative elements are disclosed in the patent and incorporated by reference herein to the extent necessary to support the present disclosure.

The present sequencer-timer 13 is a controlled sequencer that allows users to program arbitrary on-off sequences on eight to ten independent channels by means of pencil marks applied to tracks 69 upon the program card 14, FIG. 1. As is conventional, the present programmer-timer 13 has a four position front panel control switch which is first placed in a program position and the conventional reset button is pushed. The data upon the marked up program card 14, including the spaced tracks 69, is placed upon the retracted front panel slide tray 68. The tray 68 is pushed into the machine 13. This loads the program into a solid state random access memory, which serves as a working program store. The full length of the timing tracks 69 corresponds to the duration of a machine cycle, which in the illustrative embodiment has a duration of eight hours. Such cycle can be adjusted as predetermined. The cycle duration is controlled by a quartz-crystal time base.

On the output end, the programmer timer 13 provides standard outputs: AC/DC solid-state relays rated 75 mA max., 50 volts peak or reed relays 10 Watts max. An internal crystal-controlled clock cycles memory and activates output switches in compliance with the information programmed on the program input card 14 as fully disclosed in U.S. Pat. No. 4,102,492.

Timing information represented by pencil marks on the programming card 14 along the respective tracks 69 is read by photosensors or a suitable card reader. A 512-bit CMOS memory stores the coded timing information, which is correlated by a 512-bit encoder. The encoder is activated by the motion of the programming card on the sliding tray through a suitable rack and pinion arrangement.

In the illustrative embodiment, the programming card 14, FIG. 1, has 8 tracks, 69 corresponding to the corresponding 8 channels 49 directed to the individual motor means 48, FIG. 1 or solenoids 59, FIG. 4. Each of the tracks 69 correspond to individual output channels 49 so that sequencer-timer 13 or Xanadu UP-Timer, can control eight independent operations or devices. The length of each track 69 represents a duration of one complete cycle.

To program the on-off timing sequence, the operator simply darkens the desired On intervals on the card 14 upon the respective tracks 69 with a soft No. 2 pencil. The intervals thus programmed leave blank spaces. An On interval means that an output circuit controlled by the track will produce On output or contact closure during the time represented by the length of the interval.

In the illustrative embodiment, the timer controller 13 has eight channels shown individually in FIG. 2, with a group of channels bunched together at 49 in FIG. 1 for individual connection to the corresponding electronic motor means 48, FIG. 1, FIG. 3 or to the corresponding electric solenoids 59 in FIG. 4.

In the illustrative embodiment, the cycle duration is for eight hours and the timer 13 provides in the illustrative embodiment 96 time intervals corresponding to five minutes per division, for illustration. The corresponding program medium namely, the program card 14 has a corresponding 96 divisions thereon.

As indicated previously, On-Off timing sequence is generated by darkening the timing tracks 69 upon the card 14 with a soft pencil. In operation of the present sequencer-timer 13, only one channel 49 will be "On" or activated at a time. Channel TKO, FIG. 2, corresponds to the upper central electronic motor means 48 in FIG. 1, may be so controlled from the program card 14 or otherwise so as to meet the following conditions:

1. Channel TKO must be "On" when all other channels are "Off".
2. When the respective channels 1 through 7 shown in FIG. 2 are operating continuously, but alternately, channel TKO must be "On" for five minutes between "Off" and "On" times of two channels. This provides a means by which when the corresponding channels for controlling the flow of intravenous fluids are not delivering medication through any channel thereof, there will be a continuous flow of a basic or neutral solution through the delivery tube 18 to prevent clogging thereof or clotting within the catheter or needle 19, FIG. 1. The additional flow of neutral fluid through the TKO also assures that after the operation of any other individual control valve 40 there will be intermediate flow of TKO neutral solution in cleaning out the corresponding manifold tube or branch.

Having described my invention, reference should now be had to the following claims:

I claim:

1. Apparatus for administering a plurality of intravenous solutions comprising:

a solution manifold selector including a manifold plate and a valve plate sandwiched together to define a plurality of channels;

a tubing manifold having a plurality of branches for permitting the selective flow of fluids therethrough, said tubing manifold and branches being disposed in said channels;

said manifold and each of said branches having an inlet, said inlets being adapted for individual connection to the supply tube of a plurality of intravenous solution bottles respectively, and an outlet on said manifold adapted for connection to a fluid dispensing tube mounting a catheter or I.V. needle;

a plurality of spaced valve means mounted upon said valve plate, each valve means including a longitudinally adjustable element in registry with a portion of said manifold and each of said manifold branches, said elements being normally in compressive collapsing registry with the manifold and said branches closing off the flow of fluids therethrough;

electric motor means mounted upon each valve means for retracting a valve element individually opening the manifold or adjacent branch for flow of fluid therethrough, and after a predetermined period successively advancing said valve element to close off the adjacent branch or said manifold, and alternately retracting and after a time delay advancing additional individual valve elements successively in a predetermined sequence;

said valve means further comprising a threaded shaft attached to said valve element, which is advanced by rotating an internally threaded valve stem retained within said valve plate;

said motor means including a reversible electric motor mounted upon each valve means and a drive shaft; and intermeshing gear means interconnecting said drive shaft and said valve stem.

2. In the apparatus of claim 1 an electronic controllable sequencer-timer having a plurality of channel output leads connected to each motor means respectively for individually and progressively activating one motor means opening said valve means and after a predetermined time interval deactivating said motor means successively closing said valve means and progressively in accordance with a predetermined program successively activating and deactivating singly, additional motor means.

3. In the apparatus of claim 2, a program card impressed with a predetermined program removably projected into said sequencer-timer controlling progressive energization and successive deenergization of said channel output leads, respectively.

4. In the apparatus of claim 1, wherein said plurality of manifold channels comprises;

a trunk slot extending from the top to the bottom of the manifold and valve plates;

and a plurality of branch slots extending from said trunk slot to the sides of the manifold and valve plates, said branch slots extending upwardly at an acute angle to the trunk slot.

5. In the apparatus of claim 1, an intravenous supply tube connected on one end to the tubing manifold outlet and on the opposite end adapted for connection to a patient;

and a volumetric infusion pump operatively attached to the intravenous supply tube disposed between the tubing manifold outlet and the patient to pump said solutions one at a time into a patient.

6. In the apparatus of claim 5, wherein the fluid flow control valve means accurately measures fluid flow by selectively supplying the volumetric infusion pump through only one of said branches and manifold at a time for a predetermined period of time at a predetermined flow rate as set by the volumetric infusion pump.

7. In the apparatus of claim 1, a hinge interconnecting the one side edges of said manifold plate and valve plate;

and a screw means interconnecting their other side edges, to facilitate opening of said manifold plate and replacement of said tubing manifold.

8. In the apparatus of claim 3, said program card having a plurality of markable parallel spaced tracks corresponding to the number of control channels to said electric motor means respectively;

said tracks having a length corresponding to a preselected time cycle with preselected input data applied to each track;

said sequencer-timer including a solid state random access memory activated by the input data upon said program card;

and a plurality of output switches corresponding and connected to each channel respectively, selectively and progressively activating, one at a time, each motor means in compliance with data programmed upon the input program card.

9. Apparatus for administering a plurality of intravenous solutions comprising:

a solution manifold selector including a manifold plate and a valve plate sandwiched together to define a plurality of channels;

a tubing manifold having a plurality of branches for permitting the selective flow of fluids therethrough, said tubing manifold and branches being disposed in said channels;

said manifold and each of said branches having an inlet, said inlets being adapted for individual connection to the supply tube of a plurality of intravenous solution bottles respectively, and an outlet on said manifold adapted for connection to a fluid dispensing tube mounting a catheter or I.V. needle;

a plurality of spaced valve means mounted upon said valve plate, each valve means including a longitudinally adjustable element in registry with a portion of said manifold and each of said manifold branches, said elements being normally in compressive collapsing registry with the manifold and said branches closing off the flow of fluids therethrough;

electric motor means mounted upon each valve means for retracting a valve element individually opening the manifold or adjacent branch for flow of fluid therethrough, and after a predetermined period successively advancing said valve element to close off the adjacent branch or said manifold, and alternately retracting and after a time delay advancing additional individual valve elements successively in a predetermined sequence; and an electronic controllable sequencer-timer having a plurality of channel output leads connected to each motor means respectively for individually and progressively activating one motor means opening said valve means and after a predetermined time interval deactivating said motor means successively closing said valve means and progressively in accordance with a predetermined program successively activating and deactivating singly, additional motor means;

said valve means further comprising a threaded shaft attached to said valve element, which is advanced by rotating an internally threaded valve stem retained within said valve plate.

10. In the apparatus of claim 9, an intravenous supply tube connected at one end to the tubing manifold outlet and on the opposite end adapted for connection to a patient;

and a volumetric infusion pump operatively attached to the intravenous supply tube disposed between the tubing manifold outlet and the patient to pump said solutions into a patient.

11. In the apparatus of claim 10, an upright tube support adjustably mounted upon a standard;

clamp means upon said manifold selector adjustably secured to said tube support;

bracket means upon said sequencer-timer overlying and secured to said tube support;

and clamp means upon said infusion pump adjustably secured to said tube support.

12. Apparatus for administering a plurality of intravenous solutions comprising;

a solution manifold selector including a manifold plate and a valve plate sandwiched together to define a plurality of channels;

a tubing manifold having a plurality of branches for permitting the selective flow of fluids therethrough, said tubing manifold and branches being disposed in said channels;

said manifold and each of said branches having an inlet, said inlets being adapted for individual connection to the supply tube of a plurality of intravenous solution bottles respectively, and an outlet on said manifold adapted for connection to a fluid dispensing tube mounting a catheter or I.V. needle;

a plurality of spaced valve means mounted upon said valve plate, each valve means including a longitudinally adjustable element in registry with a portion of said manifold and each of said manifold branches, said elements being normally in compressive collapsing registry with the manifold and said branches closing off the flow of fluids therethrough;

electric motor means mounted upon each valve means for retracting a valve element individually opening the manifold or adjacent branch for flow of fluid therethrough, and after a predetermined period successively advancing said valve element to close off the adjacent branch or said manifold, and alternately retracting and after a time delay advancing additional individual valve elements successively in a predetermined sequence;

an electronic controllable sequencer-timer having a plurality of channel output leads connected to each motor means respectively for individually and progressively activating one motor means opening said valve means and after a predetermined time interval deactivating said motor means successively closing said valve means and progressively in accordance with a predetermined program successively activating and deactivating singly, additional motor means;

said valve means further comprising a threaded shaft attached to said valve element, which is advanced by rotating an internally threaded valve stem retained within said valve plate;

said motor means including a reversible electric motor mounted upon each valve means and a drive shaft; and intermeshing gear means interconnecting said drive shaft and said valve stem.

* * * * *